United States Patent [19]

Wilson, II

[11] Patent Number: 4,890,609
[45] Date of Patent: Jan. 2, 1990

[54] AIR-DIRECTING APPARATUS FOR AIR MASK

[76] Inventor: Robert H. Wilson, II, 236 S. Carol Blvd., Upper Darby, Pa. 19082

[21] Appl. No.: 211,712

[22] Filed: Jun. 27, 1988

[51] Int. Cl.⁴ ............................................. A61M 16/06
[52] U.S. Cl. ..................................... 128/206.29; 2/9; 128/206.28
[58] Field of Search ........................ 128/207.12, 206.28, 128/206.29, 207.12, 202.27; 2/206, 9, 173; 446/27

[56] References Cited

U.S. PATENT DOCUMENTS

| | | | |
|---|---|---|---|
| 596,919 | 1/1898 | Steves | 128/206.29 |
| 835,075 | 11/1906 | Mahaffy | 128/207.12 |
| 996,135 | 6/1911 | Poe | 128/206.29 |
| 1,366,392 | 1/1921 | Lamb | 128/207.12 |
| 1,395,948 | 11/1921 | Drager | 128/206.29 |
| 1,978,994 | 10/1934 | Fortunato | 128/206.29 |
| 2,383,649 | 8/1945 | Heidbrink | 128/206.29 |
| 2,619,085 | 11/1952 | Bradley | 128/207.12 |
| 3,357,426 | 12/1967 | Cohen | 128/202.27 |
| 3,602,219 | 8/1971 | Warncke | 128/201.15 |
| 4,573,463 | 3/1986 | Hall | 128/206.29 |
| 4,655,213 | 4/1987 | Rapoport et al. | 128/207.12 |

Primary Examiner—Edgar S. Burr
Assistant Examiner—Huong Q. Pham
Attorney, Agent, or Firm—Lipton, Famiglio & Elman

[57] ABSTRACT

This invention is a device for orally directing air while wearing an air mask. In the invention, a tube extends from outside the air mask, through the air mask, and into the mask wearer's mouth. The tube is fitted with means to seal its passage through the mask and may also include a one-way valve to prevent aspiration through it. In a preferred embodiment, the invention is manufactured separately from an air mask and may be reused after the air mask becomes worn out.

3 Claims, 2 Drawing Sheets

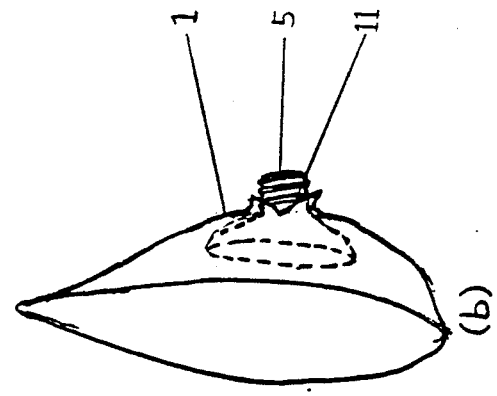
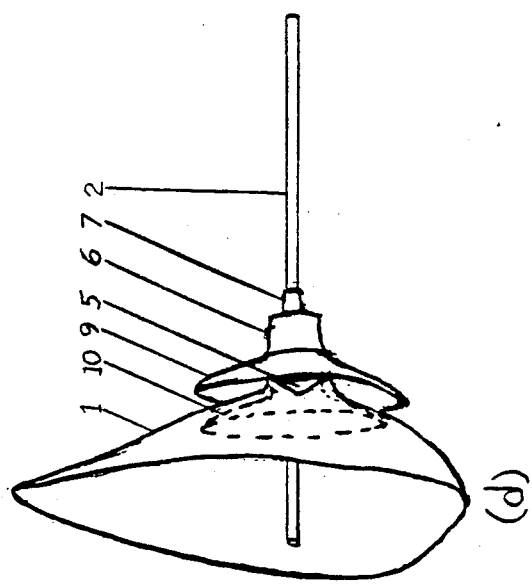
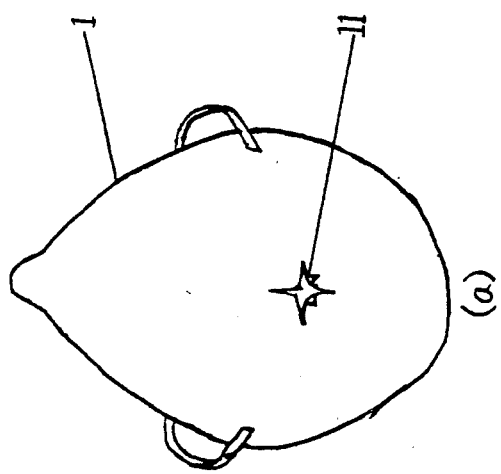
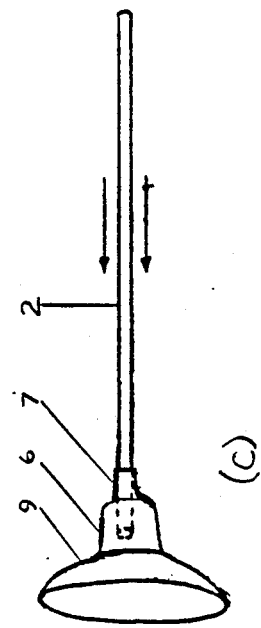
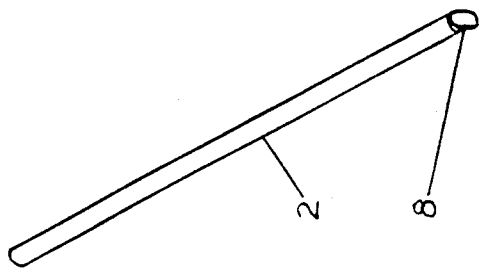
FIG. 4
FIG. 3

AIR-DIRECTING APPARATUS FOR AIR MASK

BACKGROUND OF THE INVENTION

This invention relates to protective masks, respiratory masks, and air masks, and more particularly to masks worn to prevent aspiration of dust, sawdust, and other irritants.

Various dust and irritant masks have been developed in recent years to prevent inhalation of sawdust, asbestos, and other irritants. These masks fail to serve that purpose; however, if mask wearers must remove them while working. Existing mask designs fail to accommodate the mask wearer's ordinary need to blow away dirt or sawdust.

Typically, these masks are made of air-permeable material and provide only space for a person's nose and mouth and means for sealing the mask against the person's face. A respiratory mask may also include an attached hose for connection to a supply of oxygen or an anesthetic. The prior art does not disclose an apparatus allowing a mask wearer to direct air toward a workpiece or work surface while maintaining the protection of the mask.

SUMMARY OF THE INVENTION

Carpenters and other workers often need to remove dust from their workpiece or work surface while using tools. Woodworking tools, for example, leave sawdust that should be removed from the workpiece or surface while the tools are being used. The user, would like to blow the dust away but does not wish to aspirate the sawdust or to stop working to brush the dust away with his or her hands. The applicant's invention prevents aspiration of dust and other irritants but allows the user to blow the dust away from a workpiece or surface.

The present invention may be used with a variety of air masks. In this invention, a tube extends through an air mask into the mask wearer's mouth. In a preferred embodiment, the tube is attached to outside sealing means that connect to sealing means on the inside of the mask near the mask wearer's mouth. After the air mask becomes worn, the wearer may remove the air-directing apparatus and use it with a new air mask. In an alternative embodiment, the aforementioned tube includes a one-way valve to prevent aspiration of dust through the tube.

Accordingly, an object of this invention is to provide an apparatus allowing one to orally direct air for blowing away dust while wearing an air mask.

Another object of this invention is to provide an air-directing apparatus that may be reused after an air mask is worn out.

BRIEF DESCRIPTION OF THE DRAWINGS

FIG. 3 is a perspective view of the tube of the invention showing a one-way flapper valve to prevent aspiration of dust through the tube FIG. 4 (a), (b), (c), and (d) show a method of attaching the air-directing apparatus to an existing air mask.

DETAILED DESCRIPTION OF PREFERRED EMBODIMENTS

Figure 1:
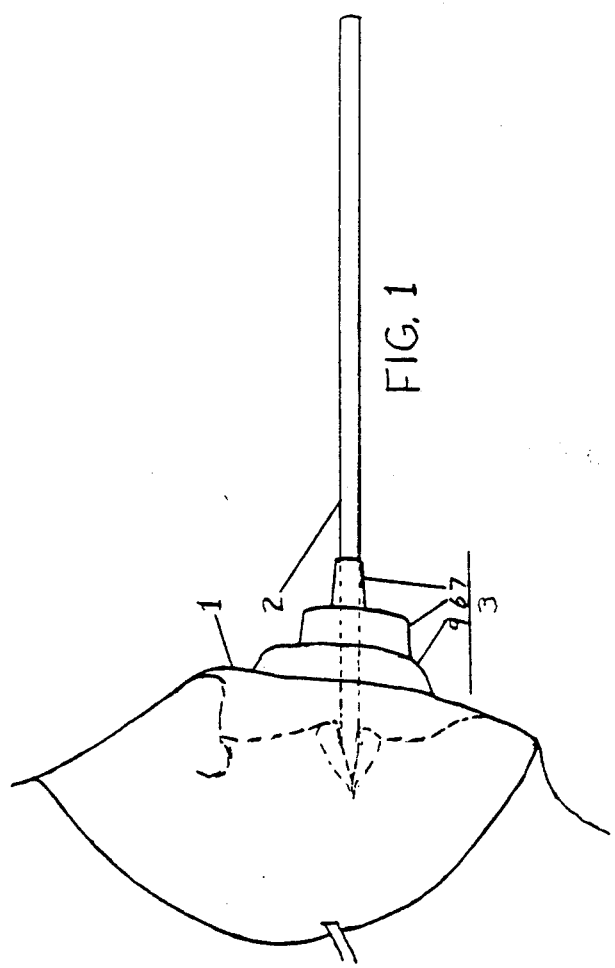
FIG. 1 is a side view of the invention as worn with an air mask.

FIG. 1 shows the air mask 1, tube 2, and outside connecting means 3. As shown, the air mask 1 fits over the mask wearer's nose and mouth and adheres to his or her face. The tube 2 extends from outside the air mask through outside sealing means 3 and into the user's mouth. By this configuration, air mask 1 prevents the user from aspirating the dust and other irritants while tube 2 allows the user to blow them away.

Sealing means 3 shown in FIG. 1 has 3 parts: washer 9, threaded portion 6, and sleeve 7. Washer 9 is used to help seal an opening in air mask 1 and may be separate from or rigidly connected to threaded portion 6.

Figure 2:
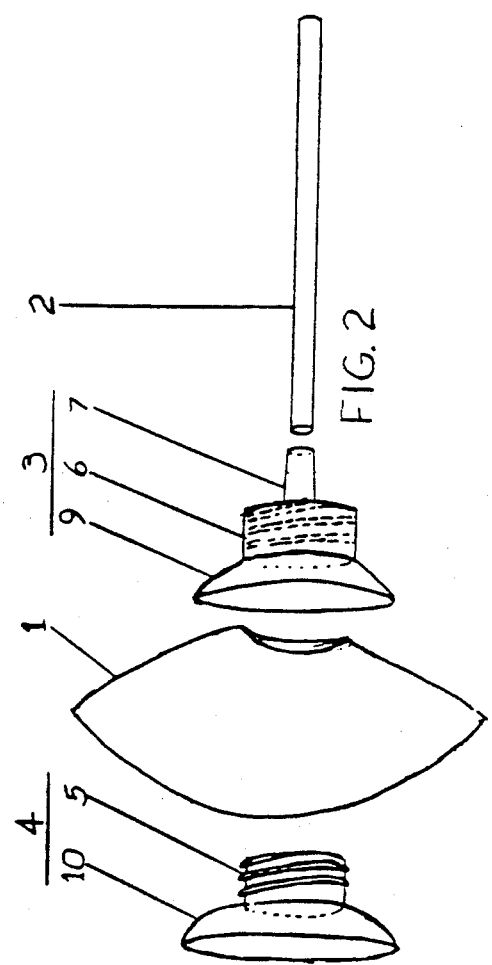
FIG. 2 is an exploded view of a preferred embodiment of the invention.

FIG. 2 is an exploded view showing the various parts of the invention. Sealing means 3 and 4 are hollow, and they may be made of plastic, metal, or many other materials. In this embodiment, the washer 9, threaded portion 6, and sleeve 7 of outside sealing means 3 are rigidly connected. Inside sealing means 4 are comprised of washer 10 and threaded portion 5, which are rigidly connected.

Air mask 1 may be any one of several varieties currently available. Air mask 1 fits over inside sealing means 4 so that threaded portion 5 extends through air mask 1. Outside sealing means 3 fit over air mask 1 so that threaded portion 6 cooperatively engages threaded portion 5.

Tube 2 fits snugly inside sleeve 7 and is held in place by friction between the outside surface of tube 2 and the inside surface of sleeve 7. In alternative embodiments (not shown), sealing means 3 or 4 may have a narrow passage that frictionally engages tube 2 to hold it in place.

FIG. 3 is a perspective view of the tube 2 in an alternative embodiment. In this alternative embodiment, a one-way flapper valve 8 is attached to the tube 2 to prevent aspiration of dust through the tube 2. By this configuration, the user may still blow air through tube 2, but cannot inhale dust through the open end of tube 2.

It is contemplated that the air-directing apparatus disclosed herein may be manufactured and sold separately from air masks. Accordingly, a method of attaching the apparatus to previously manufactured air masks is necessary.

FIGS. 4(a), (b), (c) and (d) demonstrate a method of attaching the air-directing apparatus to an air mask. First, an X-cut 11 is made just below the center of the air mask 1, as shown in FIG. 6(a). Second, threaded portion 5 of inside sealing means 4 is pushed through the concave side of air mask 1, as shown in FIG. 6(b). Third, in FIG. 6(c), tube 2 is pushed through sleeve 7 of outside sealing means 3. Fourth, threaded portions 5 and 6 are screwed together. Washers 9 and 10 seal X-cut 11 outside threaded portions 5 and 6.

Using this method, the air-directing apparatus can be attached to any existing air mask and later removed when the mask becomes worn. Thus, the more sturdy air-directing apparatus may be reused with other masks.

There are various changes and modifications that may be made to applicant's invention, as would be apparent to those skilled in the art. However, any of these changes or modifications are included in the teaching of applicant's disclosure, and it is intended that the present invention be limited only by the scope of claims appended hereto.

What is claimed is:

1. An apparatus for orally directing air through a face mask to remove dust from a work piece or work surface, comprising:
    (a) a face mask having a convex outer surface and a concave inner surface made of an air-permeable material thereby preventing a wearer from inhaling irritants;
    (b) a tube extending from outside said mask's convex outer surface and through said mask to its concave inner surface, so that an end of said tube may be placed in a mask wearer's mouth, a one-way valve attached to said tube to prevent aspiration of dust through said tube; and
    (c) means for attaching and sealing said tube to said mask said means comprising concentric threaded members sealingly engaging both said outer and said inner surfaces of said face mask; so that the mask wearer may orally direct air away from a workpiece or surface by blowing through said tube.

2. The apparatus of claim 1 wherein said attaching and sealing means comprise:
    (a) a first sealing member fitting inside the air mask's concave side and extending through the air mask to its concave side; and
    (b) a second sealing member cooperatively engageable to said first sealing member and fitting on the air mask's convex side.

3. A method of attaching an air-directing apparatus to an air mask to remove dust from a work piece or work surface, comprising the steps of:
    (a) cutting an X-shaped opening in the air mask;
    (b) passing first means for attaching the apparatus through the opening from a first side of the air mask, so that a portion of the attaching means extends from a second side of the air mask;
    (c) threadably securing second attaching means to the first attaching means, so that the second attaching means seal the opening in the air mask except inside the first attaching means;
    (d) inserting a tube through said first and second attaching means, so that the tube extends beyond the first and second attaching means; so that a person may blow through the tube while wearing the air mask; and
    (e) positioning a one-way valve on said tube to prevent aspiration of dust through said tube.

* * * * *

UNITED STATES PATENT AND TRADEMARK OFFICE
CERTIFICATE OF CORRECTION

PATENT NO. : 4,890,609

DATED : January 2, 1990

INVENTOR(S) : Robert H. Wilson, II

It is certified that error appears in the above-identified patent and that said Letters Patent is hereby corrected as shown below:

Claim 2, column 4, line 3 after the word "its" the word "concave" should be deleted and the word "convex" should be inserted in its stead.

Signed and Sealed this

Nineteenth Day of May, 1992

Attest:

DOUGLAS B. COMER

Attesting Officer

Acting Commissioner of Patents and Trademarks